(12) United States Patent
Robinson

(10) Patent No.: US 6,410,322 B1
(45) Date of Patent: Jun. 25, 2002

(54) ANTISENSE OLIGONUCLEOTIDE INHIBITION OF VASCULAR ENDOTHELIAL GROWTH FACTOR EXPRESSION

(76) Inventor: Gregory S. Robinson, 194 School St., Acton, MA (US) 01720

( * ) Notice: Subject to any disclaimer, the term of this patent is extended or adjusted under 35 U.S.C. 154(b) by 0 days.

(21) Appl. No.: 08/098,942

(22) Filed: Jul. 27, 1993

(51) Int. Cl.$^7$ ............................. C12N 5/02; C07H 21/04
(52) U.S. Cl. ...................................... 435/375; 536/24.5
(58) Field of Search .......................... 435/375; 536/24.5

(56) References Cited

U.S. PATENT DOCUMENTS

| | | | |
|---|---|---|---|
| 4,456,550 A | | 6/1984 | Dvorak et al. |
| 5,149,797 A | * | 9/1992 | Pederson et al. .......... 536/23.1 |
| 5,220,007 A | | 6/1993 | Pederson et al. |

OTHER PUBLICATIONS

Uhlmann et al. (1990) Chemical Reviews vol. 90(4) : 544–579.*
Claffey et al. (1992) J. Biol. Chem. vol. 267(23): 16317–16322.*
Tischer et al. (1991) J. Biol. Chem. vol. 266 (18) : 11947–11954.*
Foulkes et al. (1992) WO 92/13063 (Abstr. only).*
Kim et al. (1993) Nature vol. 362 : 841–844.*
Leung et al., *Science* 246, 1306 (1989).
Conn et al., *Proc. Natl. Acad. Sci. U.S.A.* 87, 2628 (1990).
Senger et al., *Cancer Res.* 50, 1774 (1990).
Brown et al., *J. Exp. Med.* 176, 1375 (1992.
Plate et al., *Nature* 359, 845 (1992).
Folkman, *J. Natl. Cancer Inst.* 82, 4 (1990).
Kerbel, *BioEssays* 13, 31 (1991).
Agrawal, *Trends in Biotech.* 10, 152 (1992).
Stephenson and Zamecnik, *Proc. Natl. Acad. Sci. U.S.A.* 75, 285 (1978).
Zamecnik and Stephenson, *Proc. Natl. Acad. Sci. U.S.A.* 75, 280 (1978).
Leonetti et al., *Gene* 72, 323 (1988).
Smith et al., *Proc. Natl. Acad. Sci. U.S.A.* 83, 2787 (1986).
Zerial et al., *Nucleic Acids. Res.* 15, 9009 (1987).
Burch and Mahan, *J. Clin. Invest.* 88, 1190 (1991).
Colige et al., *Biochemistry* 32, 7 (1993).
Monia et al., *J. Biol. Chem.* 267, 19954 (1992).
Padmapriya and Agrawal, *Bioorg. & Med. Chem. Lett.* 3, 761 (1993).
Temsamani et al., *Ann. N.Y. Acad. Sci.* 660, 318 (1992).
Tang et al., *Nucleic Acid Res.* 21, 2729 (1993).
Simons et al., *Nature* 350, 67 (1992).
Chirgwin et al., *Biochemistry* 18, 5294 (1979).
Miles and Miles, *J. Physiol. (Lond. )* 118, 228 (1952).
Brock and Capasso, *J. Cell Physiol.* 136, 54 (1988).
Karasek, *Int'l J. of Dermatology* 30, 831 (1991).
Weidner et al., *New England J. of Med.* 324, 1 (1991).
Agrawal and Leiter, *Antisense RNA and DNA*, 305–316 (1992).
Berkman, *J. of Clin. Invest.* 91, 153 (1993).
Senger et al., *Science* 219, 983 (1993).
Phillips et al., *Endocrinology* 127, 965 (1990).
Sioussat et al., *Archives of Biochem. and Biophys.* 301, 15 (1993.
Senger et al., *Cancer Research* 46, 5629 (1986).
Ferrara et al., *J. Clin. Invest.* 91, 160 (1993).
Berse et al., *Mol. Biol. of the Cell* 3, 211 (1992).
Brown et al., *Kidney Int'l* 42, 1457 (1992).
Folkman and Shing, *J. Biol. Chem.* 267, 1093 (1992).
Ratajcazk et al., *Proc. Natl. Acad. Sci. U.S.A.* 89, 11823 (1992).
Itoh et al., *Biochem. and Biophys. Res. Comm.* 188, 1205 (1992).
Yokozaki et al., *Cancer Res.* 53, 868 (1993).
Chiang et al., *J. Biol. Chem.* 266, 18162 (1991).
Gewirtz and Calabretta, *Science* 242, 1303 (1988).
Whitsell et al., *Antisense Research and Development* 1, 343 (1991).
Neckers, *Critical Rev. in Oncogenesis* 3, 175 (1992).
Lallier and Bronner–Fraser, *Science* 259, 692 (1993).
Kitajima et al., *Science* 258, 1792 (1992).
Sariola et al., *Science* 254, 571 (1991).
Wahlestedt et al., *Nature* 363, 260 (1993).
Houch et al., Mol. Endocrinology 5, 1806 (1991).

* cited by examiner

Primary Examiner—Terry McKelvey

(57) ABSTRACT

Vascular Endothelial Growth Factor (VEGF), also known as vascular permeability factor (VPF), has been shown to play in integral role in abnormal angiogenesis associated with a variety of pathological states. This disclosure presents compounds, compositions, and methods for inhibiting such abnormal angiogenesis. In particular, this disclosure presents several antisense oligonucleotides from 19 to 21 bases long that bind to VEGF RNA and inhibit production of the expression product. These antisense oligonucleotides are useful in the treatment of pathological states in which VEGF expression plays a role.

10 Claims, 3 Drawing Sheets

ANTISENSE OLIGONUCLEOTIDE INHIBITION OF VASCULAR ENDOTHELIAL GROWTH FACTOR EXPRESSION

BACKGROUND OF THE INVENTION

1. Field of the Invention

This invention relates to the field of antisense oligonucleotides for use in the inhibition of vascular endothelial cell growth factor (VEGF) expression.

2. Description of Related Art

Vascular endothelial cell growth factor (VEGF), also known as vascular permeability factor (VPF), is a 34–43 kDa (with the predominant species at about 45 kDa) dimeric, disulphide-linked glycoprotein synthesized and secreted by a variety of tumor and normal cells. Leung et al., *Science* 246, 1306 (1989), observed three VEGF transcripts (121, 165, and 189 amino acids long, respectively), suggesting that an alternative splicing mechanism is involved. More recently, Houck et al. discovered a fourth VEGF transcript having a length of 206 amino acids. Tischer et al., *J. Biol. Chem.* 266, 11947 (1991), have determined that the human VEGF coding region is comprised of eight exons. Furthermore, this group proved that three mRNA transcripts (encoding for the 121, 165, and 189 amino acid long peptides) were the result of alternative splicing. Transcripts analogous to the 121 and 165 amino acid polypeptides have been identified in the bovine system. Leung et al., *supra*. The transcript corresponding to the 165 amino acid transcript have also been identified in the rodent system—rat (Conn et al., *Proc. Natl. Acad. Sci. U.S.A.* 87, 2628 (1989)), guinea pig (Sanger et al., *Cancer Res.* 50, 1774 (1990)), and mouse (Claffey et al., *J. Biol. Chem.* 257, 16317 (1992)).

Tischer et al., *supra*, reported the nucleic acid sequence for three forms of human VEGF coding region. Claffey et al., *supra*, published the sequence for murine VEGF. Comparisons have revealed greater than 85% interspecies conservation of the VEGF molecule. All the alternatively spliced VEGF molecules have not been identified yet, but based on the conservation between species, they should be in the near future.

The following discussion presents several pathological states in which VEGF is involved and emphasizes the importance of VEGF as a potential target for therapeutic treatment.

Diabetic Retinopathy

Diabetic retinopathy is the leading cause of blindness among working age adults (20–64) in the United States. During the course of Diabetes Mellitus, one complication that can arise is an occlusion of the retinal veins. This venous occlusion results in the formation of microaneurysms due to the expansion of the vessel wall, hemorrhaging (leaking of blood into surrounding areas), "cotton wool" spots representing cellular exudates (i.e., cellular damage) and neovascularization of the retina extending into the vitreous, resulting in bleeding. Classic treatments for diabetic retinopathy are 1) the control of blood glucose and blood pressure and 2) pan retinal laser photocoagulation (PRP). Treatment #1 can prolong the onset of the disease depending on the diligence of the affected individual. Treatment #2 is quite effective, but can lead to additional hemorrhaging as well as damage to critical areas needed for visions (i.e., foveal fibers). Additional treatments for this disease which have less side effects would prove extremely valuable.

Recent observations have shown an increase in VEGF protein levels in retinal membranes from patients with diabetes, suggesting that this cytokine/growth factor may play an important role in the disease. The following characteristics of VEGF provide evidence that it may be an important regulator of diabetic retinopathy: (1) The action of VEGF is specific for endothelial cells; (2) VEGF has been shown to be angiogenic as well as mitogenic; (3) VEGF is a secreted molecule; (4) VEGF induces vascular permeability; and 5) VEGF is induced under hypoxic conditions (i.e., during retinal vein occlusion).

Atherosclerotic Plaque Formation

VEGF may play a role in the development of an atherosclerotic plaque. Atherosclerosis describes a state where the formation of lipid-containing lesions occurs in medium and large arteries. It is the primary cause of myocardial and cerebral infarctions in the United States. Lesions form within the intima, the innermost layer of the arterial wall, and are separated into two forms: the fatty streak (early), and the fibrous plaque (advanced). Both of these forms are characterized by lipid-filled macrophages (derived from blood-borne monocytes) and smooth muscle cells. The fibrous plaque is further characterized by the deposition of connective tissue and cholesterol crystals. These lesions occlude the lumen of the blood vessel diminishing the blood flow, leading to ischemia and necrosis. Research has shown that neovascularization can also occur in the atherosclerotic lesion. Levels of VEGF protein in these affected areas have not been determined, but it has been shown that both monocytes and macrophages express VEGF.

Wound Healing

VEGF may also be important in maintaining normal states of wound healing. See Brown et al., *J. Exp. Med.* 176, 1375 (1992). Wound healing is usually a regulated response to injury or trauma. Focal hemorrhaging is followed by the extravasation (leaking) of fibrinogen from the plasma to form a fibrin gel or clot. This initial matrix is replaced by granulation tissue (fibronectin, collagen, proteoglycan) and finally by scar tissue. In addition, keratinocytes migrate and form a covering to protect against fluid loss and bacterial infection. One major characteristic of wound healing is that vessel hyperpermeability occurs for some time after bleeding has stopped. In addition, angiogenic activity is detectable during this time period. Recent work has shown that keratinocytes, located at the border of the wound as well as in the wound covering, produce VEGF. Brown et al., *supra*. This result suggests that VEGF may be responsible for hyperpermeable and angiogenic activity associated with wound healing.

Aberrant would healing associated with surgery can result in complications such as hypertrophic scarring (excessive collagen deposition), keloid formation (scar tissue invading normal surrounding tissue), and adhesions in the peritoneal cavity. Other problems related with unregulated wound healing occur during the formation of lung fibrosis and in diabetes mellitus (wounds do not heal). It is believed that VEGF plays a role in these processes as well.

Tumor Angiogenesis

VEGF may be a tumor angiogenesis factor. Plate et al., *Nature* 359, 845 (1992). Angiogenesis is the tightly regulated processes by which new blood vessels develop. The development of a vascular system is necessary for the flow of nutrients and waste to and from tissues and organs. Smaller solid tumors (<1–2 mm) do not require an extensive vascular system to survive, but instead derive their nourishment through the diffusion of needed nutrients. However, in order for these cell masses to grow beyond several millimeters in size, additional vascularization is needed. See, e.g., Folkman, *J. Natl. Cancer Inst.* 82, 4 (1990). It has been suggested that inhibition of tumor angiogenesis might be an effective strategy to combat tumor growth and circumvent acquired resistance to traditional anti-cancer therapeutic agents. Kerbel, *BioEssays* 13, 31(1991). Kim et al., *Nature* 362, 841 (1993) reported that monoclonal antibodies specific for VEGF inhibited the growth of tumors in vivo.

The tumor stroma, which contains both connective tissue and the vascular system, is essentially the "lifeline" of the tumor. Whereas normal tissue vasculature is organized and can respond to changes in metabolism, the tumor stroma is poorly organized and closely resembles scar tissue found during wound healing. The tumor stroma may represent only a small portion of the total tumor (e.g., medullary carcinoma of the breast) or may exist as 80–90% of the total cell mass (e.g., desmoplastic carcinoma). Tumor blood vessels also differ from those found in normal tissue in that they are hyperpermeable to plasma and plasma proteins. Whereas this porosity is seen in normal tissue only during wound healing, solid tumors maintain this porous characteristic indefinitely.

While a necessary component for tumor growth, the stroma also acts as a barrier against macromolecules (e.g., monoclonal antibodies) which are needed in sufficient quantities to be effective as therapeutic agents. In large tumors, antibodies/macromolecules may not be effective due to large diffusional spaces as well as absorption into perivascular regions of peripheral tumor cells. Consequently, an alternative therapeutic compound is desirable.

As just discussed, VEGF is principal component in many pathological states and processes. Research has shown that VEGF is present in regions of tumors where capillary growth is occurring and suggests that VEGF can trigger the entire sequence of events leading to angiogenesis. By contrast, VEGF levels in normal tissues is relatively low. Regulation of the levels of VEGF expression, therefore, could prove to be an important method of treating pathological conditions without significantly affecting normal tissue. For instance, it follows from the earlier discussion that inhibition of VEGF expression may play an important role in (a) regulating the ocular complications associated with diabetic retinopathy, (b) regulating the formation of an atherosclerotic plaque, (c) controlling certain unregulated instances relating to wound healing processes, and (d) preventing and altering angiogenesis associated with tumor growth and metastasis. These, of course, are but examples of the diseased states in which VEGF is involved and for which regulation of VEGF expression could prove useful. Other pathologic states brought about (in part) by VEGF expression are also potential candidates for treatment by regulation of VEGF expression.

Antisense oligonucleotide technology may provide a novel approach to the inhibition of VEGF expression. See generally Agrawal, *Trends in Biotech*. 10, 152 (1992). By binding to the complementary nucleic acid sequence (the sense strand), antisense oligonucleotides are able to inhibit splicing and translation of RNA. In this way, antisense oligonucleotides are able to inhibit protein expression. Antisense oligonucleotides have also been shown to bind to genomic DNA, forming a triplex, and inhibit transcription. Furthermore, a 17-mer base sequence statistically occurs only once in the human genome, and thus extremely precise targeting of specific sequences is possible with such antisense oligonucleotides.

In 1978 Zamecnik and Stephenson were the first to propose the use of synthetic antisense oligonucleotides for therapeutic purposes. Stephenson and Zamecnik, *Proc. Natl. Acad. Sci. U.S.A.* 75, 285 (1978); Zamecnik and Stephenson, *Proc. Natl. Acad. Sci. U.S.A.* 75, 280 (1978). They reported that the use of a oligonucleotide 13-mer complementary to the RNA of Rous sarcoma virus inhibited the growth of the virus in cell culture. Since then, numerous other studies have been published manifesting the in vitro efficacy of antisense oligonucleotide inhibition of viral growth, e.g., vesicular stomatitis viruses (Leonetti et al., *Gene* 72, 323 (1988)), herpes simplex viruses (Smith et al, *Proc. Natl. Acad. Sci. U.S.A.* 83, 2787 (1986)), and influenza virus (Zerial et al., *Nucleic Acids Res.* 15, 9909 (1987)).

Antisense oligonucleotides have also been shown to inhibit protein expression in mammalian systems. For example, Burch and Mahan, *J. Clin. Invest.* 88, 1190 (1991), disclosed antisense oligonucleotides targeted to murine and human IL-1 receptors that inhibited IL-1-stimulated $PGE_2$ synthesis in murine and human fibroblasts, respectively; Colige et al., *Biochemistry* 32, 7 (1993) disclosed antisense oligonucleotides that specifically inhibited expression of a mutated human procollagen gene in transfected mouse 3T3 cells without inhibiting expression of an endogenous gene for the same protein; and Monia et al., *J. Biol. Chem.* 267, 19954 (1992), disclosed selective inhibition of mutant Ha-ras mRNA expression with phosphorothioate antisense oligonucleotide.

In most cases, however, unmodified antisense oligonucleotides are unsuitable for use in in vivo systems because of their susceptibility to attack by nucleases. Consequently, there has been much research in the area of modifying oligonucleotides to make them immune to such attack, thereby stabilizing the molecules for in vivo use. See generally Uhlmann and Peymann, *Chemical Reviews* 90, 543 (1990) at pages 545–561 and references cited therein. Focus has been on modifying the internucleotide phosphate residues, modifying the nucleoside units, modifying the 2' position and substituting other moieties for the internucleotide phosphate. For example, Padmapriya and Agrawal, *Bioorg. & Med. Chem. Lett.* 3, 761 (1993) disclosed synthesis of oligodeoxynucleoside methlyphosphonothioates; Temsamani et al., *Ann. N.Y. Acad. Sci.* 660, 318 (1992) disclosed certain 3' end-capped oligodeoxynucleotide phosphorothioates; and Tang et al., *Nucleic Acids Res.* 21, 2729 (1993) disclosed self-stabilized antisense oligodeoxynucleotide phosphorothioates having a hair-pin loop structure at their 3' ends.

Many modified antisense oligonucleotides are capable of withstanding nucleolytic degradation, yet are still capable of hybridizing to target sequences and, thus, inhibiting protein expression. These modified oligonucleotides are better suited for in vivo applications. Tang et al., *supra*, showed that self-stabilized antisense oligonucleotides showed greater in vivo stability than their linear counterparts in mice. Simons et al. *Nature* 359, 67 (1992) reported the use of two antisense c-myb phosphorothioate oligonucleotides that suppressed intimal accumulation of rat carotid arterial smooth muscle cells in vivo.

The oligonucleotides disclosed by Pederson et al. in U.S. Pat. No. 5,220,007 ('007) is another modified antisense oligonucleotide that may be particularly well-suited for both in vitro and in vivo inhibition of protein expression. That molecule comprises an internal sequence having two or more consecutive, modified or unmodified, phosphodiester linkages. The internal sequence is flanked on both sides by modified nucleic acid sequences. The internal sequence activates RNase H, while the flanking sequences are unable to activate RNase H. The result is that when the oligonucleotide of the '007 patent is bound to the target mRNA sequence, RNase H will excise the region of the target sequence complementary to the internal sequence of the antisense oligonucleotide. The target mRNA is thereby inactivated and protein expression inhibited.

Similarly, 3' end-capped (Temsamani et al., *supra*) and self-stabilized 3' hair-pin loop (Tang et al., *supra*) antisense oligonucleotides have been shown to have increased stability to nucleolytic attack and therefore may be well suited for inhibition of protein expression. The 3' hair-pin loop structure of Tang et al. is characterized as having a 3'-terminal sequence that is substantially complimentary and anneals to an internal sequence.

There is another convincing rational behind the use of antisense oligonucleotide inhibition of VEGF expression to control angiogenesis. Whereas macromolecules such as monoclonal antibodies may have difficulty in reaching their target site at an effective concentration, antisense oligonucleotides can more easily enter cells/cell masses and accumulate at inhibiting concentrations. Antisense inhibition of VEGF is likely to provide an important tool in altering the development of abnormal angiogenesis.

Inhibition of VEGF expression by means of antisense oligonucleotide technology will also be useful in determining the role of this cytokine in processes where angiogenesis is involved. In vitro systems which mimic blood vessel formation/permeability have been developed. The role of VEGF in these systems can be determined using antisense oligonucleotides. Other in vitro systems, in use or being designed, can benefit from this technology. There are several areas where the role of VEGF has not been determined. If inhibition of VEGF does not reduce tumor growth, it does not mean other systems (psoriasis, fertilizations-implantation, vascularization of the endometrium) should not be investigated.

SUMMARY OF THE INVENTION

Vascular Endothelial Growth Factor (VEGF) has been shown to play an integral role in angiogenesis associated with a variety of pathological conditions. An object of the present invention is to suppress angiogenesis associated with pathological conditions. A further object of the present invention is to provide useful compounds, compositions and methods for preventing the expression of VEGF associated with these states. A still further object of the present invention is to provide compounds, compositions and methods for the treatment of these pathological states.

Accordingly, this disclosure presents antisense oligonucleotides that have been constructed and are targeted to bind to nucleic acid sequences encoding VEGF, thereby blocking production of the expression product. Also presented are methods for inhibiting VEGF expression and angiogenesis using these oligonucleotides, both in vitro and in vivo.

BRIEF DESCRIPTION OF THE DRAWINGS

The foregoing and other objects of the present invention, the various features thereof, as well as the invention itself may be more fully understood from the following description, when read together with the accompanying drawings in which.

DESCRIPTION OF THE PREFERRED EMBODIMENTS

Figure 1:
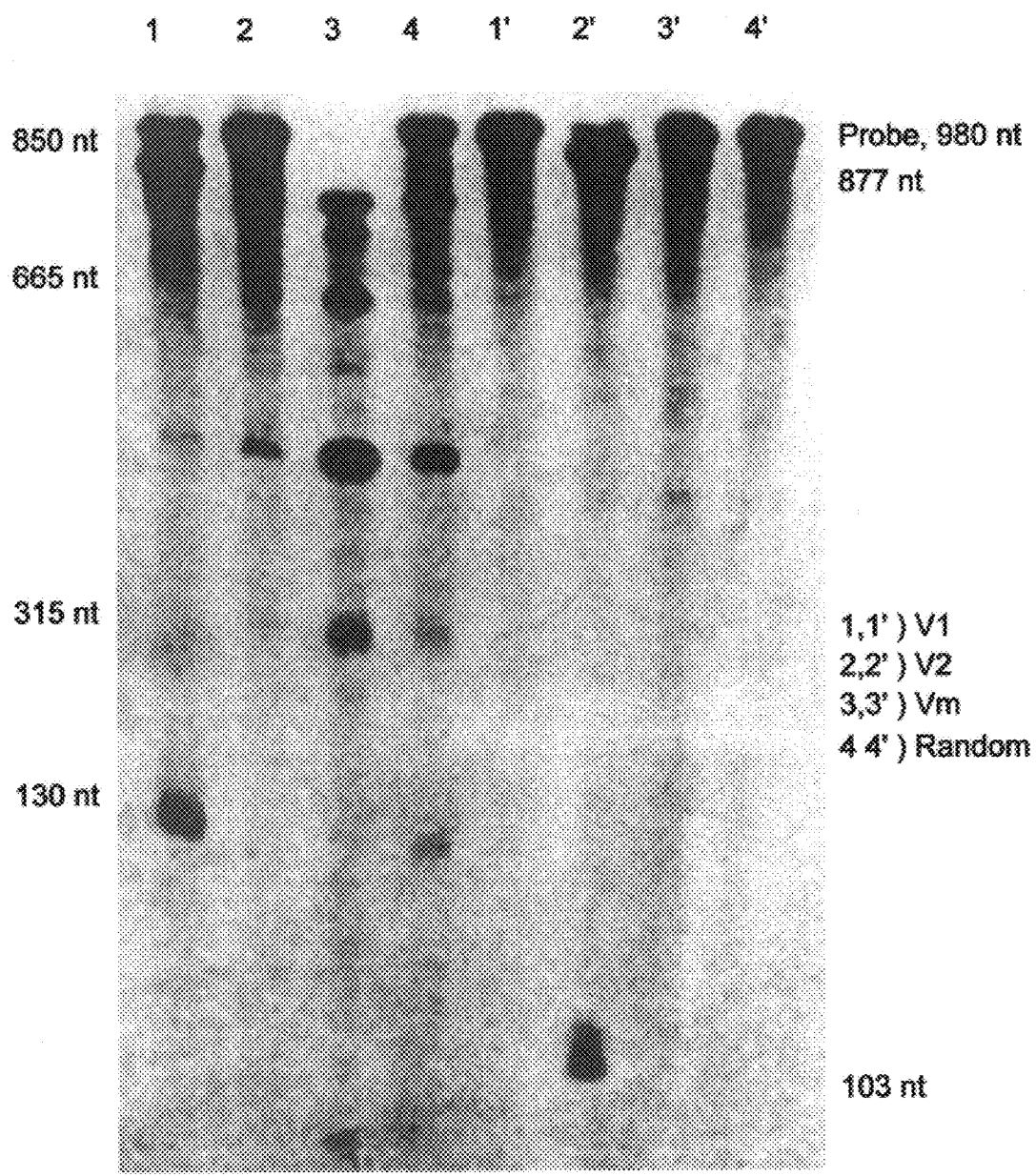
FIG. 1 shows the results of the RNase H binding assay.

Several novel antisense oligonucleotide phosphorothioates have been found that bind to murine VEGF RNA and inhibit VEGF expression in vitro. Inhibition of VEGF expression was found for antisense oligonucleotides targeted to the translational start and stop sites, as well as to internal coding regions of the VEGF mRNA. The oligonucleotides disclosed in the present invention range from 19 to 21 bases in length, but it is expected that variations in the length of the oligonucleotide can be made without substantially affecting the anti-VEGF properties of the molecule. The preferred antisense oligonucleotides of the present invention are 5'-CAGCCTGGCTCACCGCCTTGG-3' (SEQ ID NO 2) (Vm), 5'-CATGGTTTCGGAGGGCGTC-3' (SEQ ID NO 3) (JG-4), 5'-CACCCAAGAGAGCAGAAAGT-3' (SEQ ID NO 4) (JG-6), and 5'-TCGTGGGTGCAGCCTGGGAC-3' (SEQ ID NO 5) (JG-7).

Synthesis of the oligonucleotides of the present invention was done on a Pharmcia Gene Assembler series synthesizer using the phosphoamidite procedure. See, e.g., Ulhmann and Peymann at pp. 550–551 and references cited. Following assembly and deprotection, oligonucleotides were ethanol precipitated twice, dried, and resuspended in phosphate-buffered saline (1×PBS) at the desired concentration. These relatively short oligonucleotides, however, may be produced by any convenient method. Several such methods are well known in the art. See *supra*.

The nucleic acid sequence of murine VEGF is known. Claffey et al., *supra*. The sequence 5'-CAGCCTGGCTCACCGCCTTGG-3' (SEQ ID NO 2) (Vm) is targeted to the sequence surrounding the translational stop site. The sequence 5'-CATGGTTTCGGAGGGCGTC-3' (SEQ ID NO 3) (JG-4) is targeted to the sequence 5' to and containing the ATG of the translational start site of the murine VEGF molecule. The sequence 5'-CACCCAAGAGAGCAGCAGAAAGT-3' (SEQ ID NO 4) (JG-6) is targeted against sequences containing codons 2–7 of the murine VEGF molecule. The sequence 5'-TCGTGGGTGCAGCCTGGGAC-3' (SEQ ID NO 5) (JG-7) is targeted against sequences containing codons 24–29 of the murine VEGF molecule. These targeted regions of the VEGF nucleic acid sequence are conserved among all the four VEGF transcripts, resulting in complete inhibition of VEGF expression.

Positive identification of regions of the murine VEGF nucleic acid sequence whose corresponding antisense oligonucleotides inhibit VEGF expression suggests that the human antisense oligonucleotides targeted to the corresponding regions in the human VEGF nucleic acid sequence will inhibit VEGF expression in human cells. These assertions are supported by the high degree of homology between species. The corresponding human VEGF antisense oligonucleotides are 5'-CTGCCCGGCTCACCGCCTCGG-3' (SEQ ID NO: 11) (targeted to the sequence surrounding the translational stop site), 5'-CATGGTTTCGGAGGCCCGA-3' (SEQ ID NO: 12) (targeted to the sequence 5' to and containing the ATG of the translational start site of the human VEGF molecule.), 5'-CACCCAAGACAGCAGAAAGT-3' (SEQ ID NO; 13) (targeted against sequences containing codons 2–7 of the human VEGF molecule), and 5'-CCATGGGTGCAGCCTGGGAC-3' (SEQ ID NO: 17) (targeted against sequences containing codons 24–29 of the human VEGF molecule). These antisense oligonucleotides are expected to inhibit VEGF expression in human cells in much the same way as the murine antisense oligonucleotides of the present invention inhibit expression of VEGF in mouse cells.

Exon-intron boundaries are potentially useful targets for antisense inhibition of VEGF expression. With the published nucleic acid sequences and this disclosure provided, those of skill in the art will be able to identify, with only a minimum of experimentation, those antisense nucleic acid sequences that inhibit VEGF expression.

Those of skill in the art will also understand that certain modifications of internucleotide linkages of an antisense oligonucleotide can be made without negatively affecting its efficacy in the inhibition of VEGF. Indeed, some modifications may improve the efficacy of inhibition. Many types of modifications are well known to those of skill in the art and, following the teachings of this disclosure, those suitable for both in vitro and in vivo suppression of VEGF expression can be easily produced. Among the modifications contemplated by the present invention are the 3' end-capped structure, the self-stabilized 3' hair-pin loop structure, and the modification consisting of an internal RNase H-activating sequence flanked by two sequences unable to activate RNase H, all described previously. Other modified internucleotide linkages suitable for use in the present invention are the methylphosphonate and phosphoramidate linkages, which are described in Uhlmann and Peymann, *supra*. Other stabilizing modifications are also contemplated by the present invention and will be appreciated by those of skill in the art.

It is expected that in vivo inhibition of VEGF expression and abnormal angiogenesis can be achieved by administration of the antisense oligonucleotide phosphorothioates of the present invention to mammals. Administration into a mouse suffering from tumor angiogenesis can be by slow infusion pump at a rate of about 0.5–3.0 nMoles/hr (about 0.15–1.0 mg of an oligonucleotide 20-mer per kg of body weight). Alternatively, intravenous injection of about 1–5 mg of the oligonucleotide per kg body weight can be made into the tail vein. After about 10 to 21 days the tumors can be excised and analyzed for VEGF expression as well as by observing the weight and morphology of the tumors. Tumors and VEGF levels of mice treated with a control oligonucleotide can be compared. It is expected that the tumors and VEGF levels of the control mice will be larger than for the mice treated with the antisense oligonucleotides of the present invention.

There are several methods by which the effects of antisense oligonucleotides on VEGF expression can be monitored. At the RNA level, Northern blots can be performed. RNA can be obtained using the Guanidine Thiocynate method of Chirgwin et al., *Biochemistry* 18, 5294 (1979). 10 ug of total RNA are electrophoresed on a 1% formaldehyde agarose gel and transferred to a charged nylon membrane (ICN Biotrans). The membranes are probed with a $^{32}$P-labeled VEGF cDNA fragment and exposed to x-ray film.

Bioactivity can be determined by several methods, including the Miles vessel permeability assay. Miles and Miles, *J. Physiol.* (Lond). 118, 228 (1952). Hartley guinea pigs (800 g) are shaved and depilated and injected intravenously with 1.0 ml of normal saline containing 0.5 g of Evans Blue dye per 100 ml. Subcutaneous injections (250 ul) of serum-free medium containing unknown quantities of VEGF are performed. Positive (purified VEGF) and negative (normal saline) are also included in the experiment. Twenty minutes post-injection, the animals are sacrificed and the test and control sites are cut out and quantitated for extravasation of Evans Blue dye. The limit of detection for this assay is 500 pM.

Endothelial cell mitogenicity can also manifest bioactivity. In this method, human umbilical vein endothelial cells (HUVEC) are grown and maintained in EGM-UV medium (Clonetics). 1×104 cells are then plated in duplicate on 35 mM tissue culture dishes in 1.4 ml EBM medium (Clonetics) plus 5% heat-inactivated fetal bovine serum. Following cell attachment (about 4 hours), two dishes of cells are trypsinized, counted, and used for a starting cell number. Test samples containing unknown amounts of VEGF are then added in duplicate to the remaining dishes at day 0 and at day 2. Controls consisting of purified VEGF (positive) and PBS (negative) are also used. On day 4, the dishes of cells are trypsinized, counted and compared to the starting cell number. The limit of detection for this assay is 10 pM.

Intracellular calcium release is a third method of determining bioactivity. See, e.g., Brock and Capasso, *J. Cell Physiol.* 136, 54 (1988). Human umbilical vein endothelial cells (HUVEC) are maintained in EGM-UV medium. Cells are removed from the plate by means of EDTA and collagenase. The calcium-sensitive dye, Fura-2, is used to monitor changes in the concentration of intracellular calcium. In brief, medium containing an unknown concentration of VEGF is added to an aliquot of suspended HUVEC, preloaded with Fura-2. Changes in fluorescence can be measured on a Hitachi 2000 F flourometer. Positive (histamine, thrombin) and negative (EGTA) are also analyzed. (Thrombin and histamine activate phospholipase C in human endothelial cells via a phorbol ester sensitive pathway.) This method is extremely sensitive and has a limit of detection of 0.2 pM.

Those skilled in the art will recognize, or be able to ascertain, using no more than routine experimentation, numerous equivalents to the specific substances, methods, and procedures described herein. Such equivalents are considered to be within the scope of this invention, and are covered by the claims presented infra.

The following Examples are intended to illustrate, not limit, the invention.

EXAMPLE 1

RNase H Digestion Experiment

Procedure:

The murine VEGF cDNA was subcloned into the pBluescript SK+ plasmid. $^{32}$P-labeled RNA was transcribed as per manufacturer's specifications in the sense (T3 RNA polymerase) and the antisense (T7 RNA polymerase) orientations. Following phenol/CHCl$_3$ extraction and ethanol precipitation, the RNA was resuspended in T.E. Buffer (10 mM tris, pH 7.5, 1 mM EDTA, pH 8.0) and stored at −80° C. Specific activity was determined by trichloroacetic acid (TCA) precipitation.

The assay conditions were as follows:

Hybridization Conditions:
- 100–200 ng oligonucleotide
- 1 ul 10×RNase H buffer
- –50 mM Tris, pH 8.3
- –10 mM MgCl$_2$
- –50 mM KCl
- –5 mM DTT
- 1×10$^5$–10$^6$ dpm RNA
- 55°–60° C., 5 minutes
- Cool to room temperature over 30 minutes The RNA-oligonucleotide duplex was exposed to RNase H under the following conditions:
2 uM RNA-oligonucleotide duplex
1 ul 10×RNAse H buffer
0.5 ul (0.4–0.5 units) RNAse H (Pharmacia)
15 minutes at 37° C.

15 ul of formamide/bromophenol dye mix was added and analyzed by electrophoresis on a 4% Tris-Borate-EDTA (TBE) polyacrylamide gel. Following electrophoresis, the gel was dried and exposed to x-ray film for analysis.

Oligonucleotide Phosphorothioates:
V1: 5'-CAGAAAGTTCATGGTTTCGGA-3' (SEQ ID NO: 1)

V1 is an antisense oligonucleotide (21mer) targeted against the sequence surrounding the translational start site.
V2: 5'-TCCGAAACCATGAACTTTCTG-3' (SEQ ID NO: 10)

V2 is the complement (sense) oligonucleotide (21mer) to V1. It serves as a control for oligonucleotide inhibition in this experiment.
Vm: 5'-CAGCCTGGCTCACCGCCTTGG-3' (SEQ ID NO: 6)

Vm is an antisense oligonucleotide (21mer) targeted against the sequence surround the translational stop site.
R (Random): All four nucleotides at each position (21mer)

The random oligonucleotide serves as an additional oligonucleotide control for the experiment.

Analysis:

RNAse H digestion of the VEGF sense RNA hybridized with the antisense oligonucleotides was visible. See FIG. 1. The undigested probe is 980 nucleotides in length. V1 revealed the expected cleavage products of 830 and 150 nucleotides, respectively. Vm revealed expected digestion products of 665 and 315 nucleotides, respectively. Neither of the control oligonucleotides (V2, Random) resulted in any specific cleavage of the VEGF RNA. Non-specific cleavage was detected to differing degrees with all the oligonucleotides.

As a control for this experiment, these oligonucleotides were hybridized to the VEGF antisense RNA and subjected to RNAse H digestion. Only V2 resulted in cleavage of the RNA, resulting in cleavage products of 877 and 103 nucleotides. This result is expected as this oligonucleotide is sense in orientation.

This experiment shows that the antisense oligonucleotides are effective in targeting their respective sequences in the VEGF RNA, and that the resulting RNA-DNA duplex is a substrate for RNAse H digestion.

EXAMPLE 2

Antisense Oligonucleotide Inhibition of Murine VEGF Protein Expression in COS-1 Cells as Measured by Anti-VEGF Immunoprecipitation Procedure:

COS-1 cells stably expressing murine VEGF were grown in complete Dulbecco's Modified Eagles (DME) culture medium containing fetal bovine serum (10%), glutamine (2 mM), penicillin/streptomycin (100 u/100 ug), and geneticin (200 ug/ml) to a confluency of 90%. The cells were rinsed twice with serum-free DME, and then serum-free medium containing Lipofectin, a lipid-mediated carrier, at a concentration of 10 ug/ml culture medium was added. Antisense oligonucleotides were resuspended in distilled water and added dropwise to the medium resulting in the desired concentration. Oligonucleotides were re-added (in fresh DME+10% fetal calf serum containing no Lipofectin) after 16–20 hours. At 46 hours post initial oligonucleotide addition, the cells were rinsed in serum-free media lacking both methionine and cysteine and labeled for 4 hours in one milliliter of this medium containing 150–200 uCi $^{35}$S-Translabel (ICN). The labeled medium was collected, centrifuged to remove any cells and/or debris, and frozen at −80° C.

Labeled protein was precipitated in the presence of BSA (100 ug) and TCA (5%). The precipitated protein was captured on a glass fiber filter and counts were determined by means of a scintillation counter. Equal TCA-precipitable counts were immunoprecipitated overnight at 4° C. in the presence of a polyclonal anti-VEGF (human) antibody. This human antibody has been shown to cross-react with the murine VEGF protein. The antibody-VEGF complex was removed from the immunoprecipitation solution using protein A sepharose. The protein A sepharose was washed 3× in a solution containing 10 mM Tris, pH 8.0, 140 mM NaCl, 0.1% BSA, 0.1% Triton X-100, 0.01% Sodium Azide, and resuspended in 2×SDS PAGE loading buffer+7 mMDTT. The immunoprecipitated samples were electrophoresed on a 5.5%/12.5% SDS polyacrylamide gel, enhanced using Entensify solution (New England Nuclear), dried, and exposed to film.

Oligonucleotides phosphorothioates:
V1: 5'-CAGAAAGTTCATGGTTTCGGA-3' (SEQ ID NO: 1)

V1 is a antisense oligonucleotide (21mer) targeted against the sequence surrounding the translational start site.
V2: 5'-TCCGAAACCATGAACTTTCTG-3' (SEQ ID NO 10)

V2 is the complement (sense) oligonucleotide (21mer) to V1. It serves as a control for oligonucleotide inhibition in this experiment.
Vm: 5'-CAGCCTGGCTCACCGCCTTGG-3' (SEQ ID NO 6)

Vm is an antisense oligonucleotide (21mer) targeted against the sequence surrounding the translational stop site.
R (Random): All four nucleotides at each position (21 mer)

The random oligonucleotide serves as an additional oligonucleotide control for the experiment.

Figure 2:
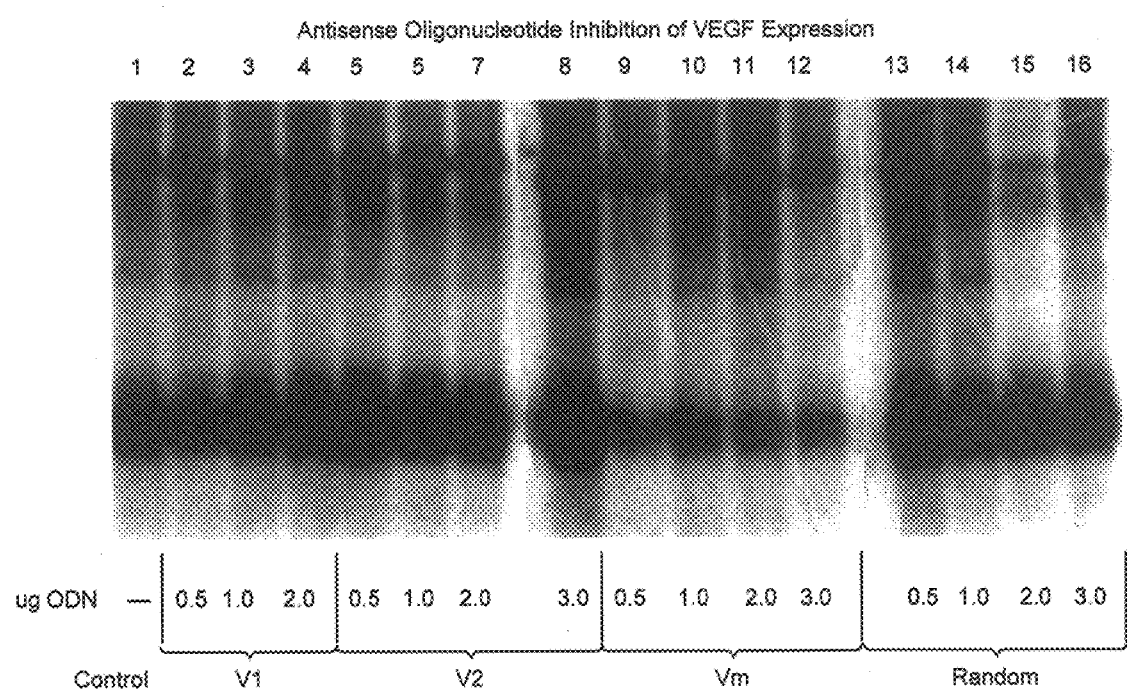
FIG. 2 shows the immunoprecipitation results of the Example 2, showing the in vitro inhibition of murine VEGF expression in transfected COS-1 cells, which stably express VEGF.

Analysis:

VEGF protein migrates as a monomer of 23 kDa under reduced conditions in an SDS polyacrylamide gel. In antisense oligonucleotide inhibition studies, it is important to show an inhibition of the active molecule, the protein. VEGF is a secreted protein, and immunoprecipitation of the protein is the most efficient means of detection. The results of this experiment (FIG. 2) show antisense oligonucleotide inhibition of murine VEGF by Vm, an oligonucleotide targeting sequences surrounding the translational stop site. Two control oligonucleotides (V2 and Random) as well as another antisense oligonucleotide (V1) do not inhibit VEGF protein expression. This final result is important as it reveals that not all antisense oligonucleotides are effective as inhibitors of VEGF.

EXAMPLE 3

Antisense Oligonucleotide Inhibition of Murine VEGF Protein Expression in NB41 Cells as Measured by Anti-VEGF Immunoprecipitation Procedure:

NB41, a murine neuroblastoma cell line which endogenously expresses murine VEGF, were grown in complete Dulbecco's Modified Eagles (DME) culture medium containing fetal bovine serum (10%), glutamine (2 mM), penicillin/streptomycin (100u/100 ug), to a confluency of 90%. The cells were refed immediately before the experiment with new culture medium. Oligonucleotides were resuspended in phosphate-buffered sale (PBS) and mixed with DOTAP (Boehringer-Manheim), a newly formulated lipofection reagent (2.5 ug/ml of culture medium), at the desired concentration. Oligonucleotides were readded (in fresh DME+10% fetal calf serum containing no DOTAP) after 16–20 hours. At 36–40 hours post initial oligonucleotide addition, the cells were rinsed in serum-free media lacking both methionine and cysteine and labeled for 4 hours in one milliliter of this medium containing 150–200 uCi $^{35}$S-Translabel (ICN). The labeled medium was collected, centrifuged to remove any cells and/or debris, and frozen at −80° C.

Labeled protein was precipitated in the presence of BSA (100 ug) and TCA (5%). The precipitated protein was captured on a glass fiber filter and counts were determined by means of a scintillation counter. Equal TCA-precipitable counts were immunoprecipitated overnight at 4° C. in the presence of a polyclonal anti-VEGF (human) antibody. This human antibody cross-reacts with the murine VEGF protein. The antibody-VEGF complex was removed from the immunoprecipitation solution using protein A sepharose. The protein A sepharose was washed 3× in a solution containing 10 mM Tris, pH 8.0, 140 mM NaCl, 0.1% BSA, 0.1% Triton X-100, 0.01% Sodium azide and resuspended in 2×SDS PAGE loading buffer +7 mM DTT. The immunoprecipitated samples were electrophoresed on a 5.5%/12.5% SDS polyacrylamide gel, enhanced using Entensify solution (New England Nuclear), dried, and exposed to film.

Oligonucleotides phosphorothioates:

JG-1: 5'-CAACGGTGACGATGATGGCA-3' (SEQ ID NO: 9)

JG1 is an antisense oligonucleotide (20mer) targeted against sequences in the 3' untranslated region of the murine VEGF molecule.

JG-3: 5'-TCGCGCTCCCTCTCTCCGGC-3' (SEQ ID NO: 8)

JG-3 is an antisense oligonucleotide (20mer) targeted against sequences in the 5' untranslated region of the murine VEGF molecule.

JG-4: 5'-CATGGTTTCGGAGGGCGTC-3' (SEQ ID NO: 3)

JG-4 is an antisense oligonucleotide (19mer) targeted against sequences 5' to and containing the ATG of the translational start site of the murine VEGF molecule.

JG-5: 5'-CAAGAGAGCAGAAAGTTCAT-3' (SEQ ID NO: 7)

JG-5 is an antisense oligonucleotide (20mer) targeted against sequences containing the ATG and extending into the coding region of the murine VEGF molecule.

JG-6: 5'-CACCCAAGAGAGCAGAAAGT-3' (SEQ ID NO: 4)

JG-6 is an antisense oligonucleotide (20mer) targeted against sequences containing codons 2–7 of the murine VEGF molecule.

JG-7: 5'-TCGTGGGTGCAGCCTGGGAC-3' (SEQ ID NO: 5)

JG-7 is an antisense oligonucleotide (20mer) targeted against sequences containing codons 24–29 of the murine VEGF molecule.

Vm: 5'-CAGCCTGGCTCACCGCCTTGG-3' (SEQ ID NO: 6)

Vm is an antisense oligonucleotide (21mer) targeted against the sequence surrounding the translational stop site.

Figure 3:
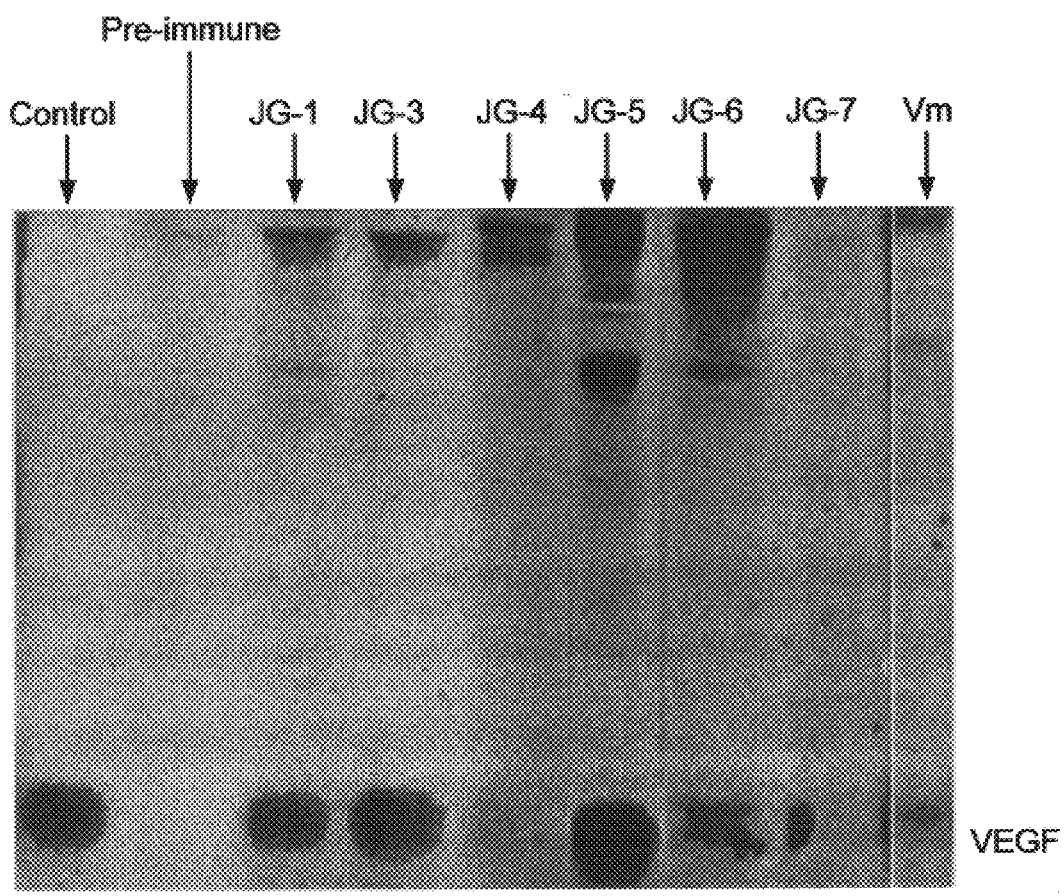
FIG. 3 shows the immunoprecipitation results of the Example 3, showing the in vitro inhibition of VEGF expression in murine NB41 cells, which endogenously express VEGF.

Analysis:

This experiment tested the activity of several oligonucleotides in inhibiting VEGF protein expression. See FIG. 3. Several of these oligonucleotides (i.e., JG-4, JG-6, JG-7) inhibit the production of VEGF protein. Other oligonucleotides (i.e., JG-1, JG-3, JG-5) have no effect on VEGF protein production. This experiment also reconfirms the inhibition seen with Vm in the previous experiment.

EXAMPLE 4

In Vivo Inhibition of VEGF Expression and Tumor Growth Rate in Murine Systems

VEGF expression and tumor growth rate inhibition may be demonstrated in the following manner. Inject tumor cell lines that are known to express VEGF subcutaneously into nude mice. Tumor formation will generally be observed within 2–3 weeks. Administer about 2.5 mg of the JG-4 antisense oligonucleotide phosphorothioate per kg body weight by intravenous injection into the tail veins of a group of 15 nude mice suffering from tumor angiogenesis. Similarly inject a control antisense oligonucleotide phosphorothioate into a group consisting of an equal number of nude mice. Follow the mice for 21 days. Excise the tumors and analyze them for weight and morphology as well as by immunohistochemical methods for VEGF expression. VEGF expression and tumor growth rate are expected to be lower in those mice receiving injections of JG-4 than in those receiving injection of the control oligonucleotide.

Similar results are expected with the JG-6, JG-7 and the Vm antisense oligonucleotide phosphorothioates.

EXAMPLE 5

Inhibition of VEGF Expression in Human Cells

Inhibition of VEGF expression in human cells may be shown in the following manner. Grow MNNG-HOS (N-methyl-N-nitro-N-nitrosoguanidine-induce osteogenic sarcoma) cells in complete Dulbecco's Modified Eagles (DME) culture medium containing fetal bovine serum (10%), glutamine (2 mM), penicillin/streptomycin (100 u/100 ug), to a confluency of 90%. Refeed the cells immediately before the experiment with new culture medium. Resuspend oligonucleotides in phosphate-buffered sale (PBS) and mix with DOTAP (Boehringer-Manheim), a newly formulated lipofection reagent (2.5 ug/ml of culture medium), at the desired concentration. Readd oligonucleotides (in fresh DME+10% fetal calf serum containing no DOTAP) after 16–20 hours. At 36–40 hours post initial oligonucleotide addition, rinse the cells in serum-free media lacking both methionine and cysteine and label for 4 hours in one milliliter of this medium containing 150–200 uCi $^{35}$S-Translabel (ICN). Collect the labeled medium, centrifuge to remove any cells and/or debris, and freeze at −80° C.

Precipitate labeled protein in the presence of BSA (100 ug) and TCA (5%). Capture the precipitated protein on a glass fiber filter and determine counts by means of a scintillation counter. Immunoprecipitate equal TCA-precipitable counts overnight at 4° C. in the presence of a polyclonal anti-VEGF (human) antibody. Remove the antibody-VEGF complex from the immunoprecipitation solution using protein A sepharose. Wash the protein A sepharose 3× in a solution containing 10 mM Tris, pH 8.0, 140 mM NaCl, 0.1% BSA, 0.1% Triton X-100, 0.01% Sodium azide and resuspended in 2×SDS PAGE loading buffer+7 mM DTT. Electorphorese the immunoprecipitated samples on a 5.5%/12.5% SDS polyacrylamide gel, enhance using Entensify solution (New England Nuclear), dry, and expose to film.

Oligonucleotide phosphorothioates:

5'-TCCGAAACCATGAACTTTCTG-3' (SEQ ID NO: 15)

This is an antisense oligonucleotide (21 mer) targeted against sequences in the 3' untranslated region of the human VEGF molecule.

5'-TCGCGCTCCCTCTCCGGCTC-3' (SEQ ID NO: 16)

This is an antisense oligonucleotide (20mer) targeted against sequences in the 3' untranslated region of the human VEGF molecule.

5'-CATGGTTTCGGAGGCCCGA-3' (SEQ ID NO 12)

This is an antisense oligonucleotide targeted to the sequence 5' to and containing the ATG of the translational start site of the human VEGF molecule.

5'-CAAGACAGCAGAAAGTTCAT-3' (SEQ ID NO: 14)

This is an antisense oligonucleotide (20mer) targeted against sequences containing ATG and coding region of the human VEGF molecule.

5'-CACCCAAGACAGCAGAAAGT-3' (SEQ ID NO: 13)

This is an antisense oligonucleotide (20mer) targeted against sequences containing codons 2–7 of the human VEGF molecule.

5'-CCATGGGTGCAGCCTGGGAC-3' (SEQ ID NO: 17)

This is an antisense oligonucleotide (20mer) targeted against sequences containing codons 24–29 of the human VEGF molecule.

5'-CTGCCCGGCTCACCGCCTCGG-3' (SEQ ID NO: 11)

This is an antisense oligonucleotide (21mer) targeted against the sequence surrounding the translational stop site.

Analysis:

This experiment tests the activity of several oligonucleotides in inhibiting VEGF protein expression. Several of these oligonucleotides, SEQ ID NOs 11–13 and 17 are expected to inhibit the production of the VEGF protein. Other oligonucleotides SEQ ID NOs 14–16 are expected to have no effect on VEGF protein production.

What is claimed is:

1. An antisense oligonucleotide having the sequence 5'-CAGCCTGGCTCACCGCCTTGG-3' (SEQ ID NO 6).

2. An antisense oligonucleotide having the sequence 5'-CATGGTTTCGGAGGGCGTC-3' (SEQ ID NO 3).

3. An antisense oligonucleotide having the sequence 5'-CACCCAAGAGAGCAGAAAGT-3' (SEQ ID NO 4).

4. An antisense oligonucleotide having the sequence 5'-TCGTGGGTGCAGCCTGGGAC-3' (SEQ ID NO 5).

5. An antisense oligonucleotide having the sequence 5'-CTGCCCGGCTCACCGCCTCGG-3' (SEQ ID NO: 11).

6. An antisense oligonucleotide having the sequence 5'-CATGGTTTCGGAGGCCCGA-3' (SEQ ID NO: 12).

7. An antisense oligonucleotide having the sequence 5'-CACCCAAGACAGCAGAAAGT-3' (SEQ ID NO: 13).

8. An antisense oligonucleotide having the sequence 5'-CCATGGGTGCAGCCTGGGAC-3' (SEQ ID NO: 17).

9. A method of inhibiting VEGF expression in vitro, comprising providing a VEGF expression-inhibiting amount of an antisense oligonucleotide complementary to VEGF mRNA in vitro, wherein the antisense oligonucleotide is chosen from the group consisting of the oligonucleotide phosphorothioates 5'-CAGCCTGGCTCACCGCCTTGG-3' (SEQ ID NO:6), 5'-CATGGTTTCGGAGGGCGTC-3' (SEQ ID NO:3), 5'-CACCCAAGAGAGCAGAAAGT-3'(SEQ ID NO:4), 5'-TCGTGGGTGCAGCCTGGGAC-3' (SEQ ID NO:5) and mixtures thereof.

10. A method of inhibiting VEGF expression in vitro, comprising providing a VEGF expression-inhibiting amount of an antisense oligonucleotide complementary to VEGF mRNA in vitro, wherein the antisense oligonucleotide is chosen from the group consisting of the oligonucleotide phosphorothioates 5'-CTGCCCGGCTCACCGCCTCGG-3' (SEQ ID NO:11), 5'-CATGGTTTCGGAGGCCCGA-3' (SEQ ID NO:12), 5'-CACCCAAGACAGCAGAAAGT-3' (SEQ ID NO:13), 5'-CCATGGGTGCAGCCTGGGAC-3' (SEQ ID NO:17) and mixtures thereof.

* * * * *

UNITED STATES PATENT AND TRADEMARK OFFICE
CERTIFICATE OF CORRECTION

PATENT NO. : 6,410,322 B1
DATED : June 25, 2002
INVENTOR(S) : Robinson

It is certified that error appears in the above-identified patent and that said Letters Patent is hereby corrected as shown below:

<u>Title page,</u>
Item [73], Assignee, should read:
-- Hybridon, Inc., Worcester, MA --.

Signed and Sealed this

Thirteenth Day of April, 2004

JON W. DUDAS
*Acting Director of the United States Patent and Trademark Office*

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (iii) HYPOTHETICAL: NO (iv) ANTI-SENSE: YES (ix) FEATURE:
      (A) NAME/KEY: misc_feature
      (B) LOCATION: 1..21
      (D) OTHER INFORMATION: /note= "phosphorothioate internucleotide linkages"

(xi) SEQUENCE DESCRIPTION: SEQ ID NO:1:

CAGAAAGTTC ATGGTTTCGG A      21

(2) INFORMATION FOR SEQ ID NO:2:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (iii) HYPOTHETICAL: NO (iv) ANTI-SENSE: YES (ix) FEATURE:
      (A) NAME/KEY: misc_feature
      (B) LOCATION: 1..21
      (D) OTHER INFORMATION: /note= "phosphorothioate internucleotide linkages"

(xi) SEQUENCE DESCRIPTION: SEQ ID NO:2:

CAGCCTGGCT CACCGCCTTG G      21

(2) INFORMATION FOR SEQ ID NO:3:

(i) SEQUENCE CHARACTERISTICS:
      (A) LENGTH: 19 base pairs (B) TYPE: nucleic acid
            (C) STRANDEDNESS: single
            (D) TOPOLOGY: linear (iii) HYPOTHETICAL: NO (iv) ANTI-SENSE: YES (ix) FEATURE:
            (A) NAME/KEY: misc_feature
            (B) LOCATION: 1..19
            (D) OTHER INFORMATION: /note= "phosphorothioate
                internucleotide linkages"

(xi) SEQUENCE DESCRIPTION: SEQ ID NO:3:

CATGGTTTCG GAGGGCGTC                                                    19

(2) INFORMATION FOR SEQ ID NO:4:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (iii) HYPOTHETICAL: NO (iv) ANTI-SENSE: YES (ix) FEATURE:
            (A) NAME/KEY: misc_feature
            (B) LOCATION: 1..20
            (D) OTHER INFORMATION: /note= "phosphorothioate
                internucleotide linkages"

(xi) SEQUENCE DESCRIPTION: SEQ ID NO:4:

CACCCAAGAG AGCAGAAAGT                                                   20

(2) INFORMATION FOR SEQ ID NO:5:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (iii) HYPOTHETICAL: NO (iv) ANTI-SENSE: YES (ix) FEATURE:
            (A) NAME/KEY: misc_feature
            (B) LOCATION: 1..20
            (D) OTHER INFORMATION: /note= "phosphorothioate
                internucleotide linkages"

(xi) SEQUENCE DESCRIPTION: SEQ ID NO:5:

TCGTGGGTGC AGCCTGGGAC                                                   20

(2) INFORMATION FOR SEQ ID NO:6:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (iii) HYPOTHETICAL: NO (iv) ANTI-SENSE: YES (ix) FEATURE:
            (A) NAME/KEY: misc_feature (B) LOCATION: 1..21
            (D) OTHER INFORMATION: /note= "phosphorothioate
                internucleotide linkages"

(xi) SEQUENCE DESCRIPTION: SEQ ID NO:6:

CAGCCTGGCT CACCGCCTTG G                                              21

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: NO (iv) ANTI-SENSE: YES (ix) FEATURE:
        (A) NAME/KEY: misc_feature
        (B) LOCATION: 1..20
        (D) OTHER INFORMATION: /note= "phosphorothioate
            internucleotide linkages"

(xi) SEQUENCE DESCRIPTION: SEQ ID NO:7:

CAAGAGAGCA GAAAGTTCAT                                                20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: NO (iv) ANTI-SENSE: YES (ix) FEATURE:
        (A) NAME/KEY: misc_feature
        (B) LOCATION: 1..20
        (D) OTHER INFORMATION: /note= "phosphorothioate
            internucleotid linkages"

(xi) SEQUENCE DESCRIPTION: SEQ ID NO:8:

TCGCGCTCCC TCTCTCCGGC                                                20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: NO (iv) ANTI-SENSE: YES (ix) FEATURE:
        (A) NAME/KEY: misc_feature
        (B) LOCATION: 1..20
        (D) OTHER INFORMATION: /note= "phosphorothioate
            internucleotide linkages"

(xi) SEQUENCE DESCRIPTION: SEQ ID NO:9:

CAACGGTGAC GATGATGGCA                                                20

(2) INFORMATION FOR SEQ ID NO:10:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (iii) HYPOTHETICAL: NO (iv) ANTI-SENSE: NO (ix) FEATURE:
    (A) NAME/KEY: misc_feature
    (B) LOCATION: 1..21
    (D) OTHER INFORMATION: /note= "phosphorothioate
        internucleotide linkages"

(xi) SEQUENCE DESCRIPTION: SEQ ID NO:10:

TCCGAAACCA TGAACTTTCT G                                        21

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: YES (iv) ANTI-SENSE: YES (ix) FEATURE:
        (A) NAME/KEY: misc_feature
        (B) LOCATION: 1..21
        (D) OTHER INFORMATION: /note= "phosphorothioate
            internucleotide linkages"

(xi) SEQUENCE DESCRIPTION: SEQ ID NO:11:

CTGCCCGGCT CACCGCCTCG G                                        21

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (iii) HYPOTHETICAL: YES (iv) ANTI-SENSE: YES (ix) FEATURE:
        (A) NAME/KEY: misc_feature
        (B) LOCATION: 1..19
        (D) OTHER INFORMATION: /note= "phosphorothioate
            internucleotide linkages"

(xi) SEQUENCE DESCRIPTION: SEQ ID NO:12:

CATGGTTTCG GAGGCCCGA                                           19

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: YES (iv) ANTI-SENSE: YES (ix) FEATURE:
        (A) NAME/KEY: misc_feature
        (B) LOCATION: 1..20
        (D) OTHER INFORMATION: /note= "phosphorothioate
            internucleotide linkages"

(xi) SEQUENCE DESCRIPTION: SEQ ID NO:13:

CACCCAAGA CAGCAGAAAGT                                                    20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: YES (iv) ANTI-SENSE: YES (ix) FEATURE:
        (A) NAME/KEY: misc_feature
        (B) LOCATION: 1..20
        (D) OTHER INFORMATION: /note= "phosphorothioate
            internucleotide linkages"

(xi) SEQUENCE DESCRIPTION: SEQ ID NO:14:

CAAGACAGCA GAAAGTTCAT                                                    20

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: YES (iv) ANTI-SENSE: YES (ix) FEATURE:
        (A) NAME/KEY: misc_feature
        (B) LOCATION: 1..21
        (D) OTHER INFORMATION: /note= "phosphorothioate
            internucleotide linkages"

(xi) SEQUENCE DESCRIPTION: SEQ ID NO:15:

TCCGAAACCA TGAACTTTCT G                                                  21

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: YES (iv) ANTI-SENSE: YES (ix) FEATURE:
        (A) NAME/KEY: misc_feature
        (B) LOCATION: 1..20
        (D) OTHER INFORMATION: /note= "phosphorothioate
            internucleotide linkages"

(xi) SEQUENCE DESCRIPTION: SEQ ID NO:16:

TCGCGCTCCC TCTCCGGCTC                                                    20

(2) INFORMATION FOR SEQ ID NO:17:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (iii) HYPOTHETICAL: YES (iv) ANTI-SENSE: YES (ix) FEATURE:
       (A) NAME/KEY: misc_feature
       (B) LOCATION: 1..20
       (D) OTHER INFORMATION: /note= "phosphorothioate
             internucleotide linkages"

(xi) SEQUENCE DESCRIPTION: SEQ ID NO:17:

CCATGGGTGC AGCCTGGGAC                                                      20